US009841372B2

(12) United States Patent
Freudenthal et al.

(10) Patent No.: US 9,841,372 B2
(45) Date of Patent: Dec. 12, 2017

(54) UNAMBIGUOUS RETARDANCE MEASUREMENT

(71) Applicant: Hinds Instruments, Inc., Hillsboro, OR (US)

(72) Inventors: John Freudenthal, Hillsboro, OR (US); Baoliang Wang, Portland, OR (US)

(73) Assignee: Hinds Instruments, Inc., Hillsboro, OR (US)

( * ) Notice: Subject to any disclaimer, the term of this patent is extended or adjusted under 35 U.S.C. 154(b) by 133 days.

(21) Appl. No.: 14/866,612

(22) Filed: Sep. 25, 2015

(65) Prior Publication Data

US 2016/0091416 A1    Mar. 31, 2016

Related U.S. Application Data

(60) Provisional application No. 62/055,140, filed on Sep. 25, 2014.

(51) Int. Cl.
G01J 4/00 (2006.01)
G01N 21/21 (2006.01)
G01N 21/23 (2006.01)

(52) U.S. Cl.
CPC ............. *G01N 21/21* (2013.01); *G01N 21/23* (2013.01)

(58) Field of Classification Search
CPC .................................. G01J 4/00; G01N 21/21
USPC ........................................................ 356/364
See application file for complete search history.

(56) References Cited

U.S. PATENT DOCUMENTS

| 6,985,227 B2 * | 1/2006 | Wang ........................ G01J 4/04 356/364 |
| 7,385,696 B2 * | 6/2008 | Wang ...................... G01N 21/23 356/364 |
| 8,542,356 B2 * | 9/2013 | Fiolka ................ G01M 11/0257 356/364 |
| 2006/0187452 A1 | 8/2006 | Wang et al. |
| 2008/0074649 A1 | 3/2008 | Levenson et al. |

FOREIGN PATENT DOCUMENTS

| TW | 201018888 | 5/2010 |
| WO | WO 2012/118079 | 9/2012 |

OTHER PUBLICATIONS

International Search Report and Written Opinion for related International Application No. PCT/US2015/052439, 6 pages, dated Feb. 4, 2016.

* cited by examiner

*Primary Examiner* — Roy M Punnoose
(74) *Attorney, Agent, or Firm* — Klarquist Sparkman, LLP

(57) ABSTRACT

This invention is directed to methods of unambiguously measuring the absolute retardance, $\delta_A$ of an optical sample. A method for measuring absolute retardance of an optical sample includes directing light comprising a plurality of wavelengths through a polarization state generator source, the optical sample, and a polarization state analyzer, detecting, at an imaging device, retardance measurement light emanating from the optical sample after also passing through the polarization state analyzer at the plurality of wavelengths, determining a measurement retardance associated with the detected retardance measurement light at each of the wavelengths, and determining an absolute retardance associated with the optical sample based on the measurement retardances determined at each of the wavelengths.

20 Claims, 11 Drawing Sheets

FIG. 5A

| (1a) Range | (1b) | (2) Dgr = Rg − Rr | (3) Sgr = Rg + Rr | (4) Calc | (5) conditions |
|---|---|---|---|---|---|
| 0 to Wg/2 | 0–265 | Dgr = 0 | 0 ~ 530 | (Rg + Rr)/2 | Dgr = 0; Ar = Ag (At all other points where Dgr = 0, Ar and Ag differ by 90; one up, one down) |
| Wg/2 to Wr/2 | 265–315 | 0 to −100 | Sgr = 530 | (Rr + Wg − Rg)/2 | Sgr = 530; |
| 0.5Wr to Wg | 315–530 | Dgr = −100 | 530 to 100 | (Wg + Wr − Rg − Rr)/2 | Dgr = −100; Ar = Ag (At all other points where Dgr = −100, Ar and Ag differ by 90; one up, one down) |
| Wg to Wr | 530–630 | −100 to 100 | Sgr = 100 | (Wg + Rg + Wr − Rr)/2 | Sgr = 100; Ar = Ag (one up one down and Ar differs Ag by 90) |
| 1Wr to 1.5Wg | 630–795 | Dgr = 100 | 100 to 430 | (Wg + Rg + Wr + Rr)/2 | Dgr = 100; Ar = Ag |
| 1.5Wg to 1.5Wr | 795–945 | 100 to −200 | Sgr = 430 | (2Wg − Rg + Wr + Rr)/2 | Sgr = 430; Ar = Ag (one up one down and Ar differs Ag by 90) |
| 1.5Wr to 2Wg | 945–1060 | Dgr = −200 | 430 to 200 | (2Wg − Rg + 2Wr − Rr)/2 | Dgr = −200; Ar = Ag |
| 2Wg to 2Wr | 1060–1260 | −200 to 200 | Sgr = 200 | (2Wg + Rg + 2Wr − Rr)/2 | Sgr = 200; Ar = Ag (one up one down and Ar differs Ag by 90) |
| 2Wr to 2.5Wg | 1260–1325 | Dgr = 200 | 200 to 330 | (2Wg + Rg + 2Wr + Rr)/2 | Dgr = 200; Ar = Ag |

FIG. 5B

| | | | | |
|---|---|---|---|---|
| 2.5Wg to 2.5Wr | 1325-1575 | 200 to -300 | Sgr = 330 | (3Wg - Rg + 2Wr + Rr)/2 | Sgr = 330<br>Ar ≠ Ag (one up one down and Ar differs Ag by 90) |
| 2.5Wr to 3Wg | 1575-1590 | Dgr = -300 | 330 to 300 | (3Wg - Rg + 3Wr - Rr)/2 | Dgr = -300; Ar = Ag |
| 3Wg to 3.5Wg | 1590-1855 | -300 to 230 | Sgr = 300 | (3Wg + Rg + 3Wr - Rr)/2 | Sgr = 300; Ar ≠ Ag (one up one down and Ar differs Ag by 90) |
| 3.5Wg to 3Wr | 1855-1890 | Dgr = 230 | 300 to 230 | (4Wg - Rg + 3Wr - Rr)/2 | Dgr = 230; Ar = Ag |
| 3Wr to 4Wg | 1890-2120 | 230 to -230 | Sgr = 230 | (4Wg - Rg + 3Wr + Rr)/2 | Sgr = 230; Ar ≠ Ag (one up one down and Ar differs Ag by 90) |
| 4Wg to 3.5Wr | 2120-2205 | Dgr = -230 | 230 to 400 | (4Wg + Rg + 4Wr - Rr)/2 | Dgr = -230; Ar = Ag |
| 3.5Wr to 4.5 Wg | 2205-2385 | -230 to 130 | Sgr = 400 | (4Wg + Rg + 4Wr + Rr)/2 | Sgr = 400<br>Ar ≠ Ag (one up one down and Ar differs Ag by 90) |
| 4.5Wg to 4Wr | 2385-2520 | Dgr = 130 | 400 to 130 | (5Wg - Rg + 4Wr - Rr)/2 | Dgr = 130; Ar = Ag |
| 4Wr to 5Wg | 2520-2650 | 130 to -130 | Sgr = 130 | (5Wg - Rg + 4Wr + Rr)/2 | Sgr = 130; Ar ≠ Ag (one up one down and Ar differs Ag by 90) |
| 5Wg to 4.5 Wr | 2650 to 2835 | Dgr = -130 | 130 to 500 | (5Wg + Rg + 4Wr + Rr)/2 | Dgr = -130; Ar = Ag |
| 4.5Wr to 5.5 Wg | 2835 to 2915 | -130 to 30 | Sgr = 500 | (5Wg + Rg + 5Wr - Rr)/2 | Sgr = 500; Ar ≠ Ag |
| 5.5Wg to 5Wr | 2915 - 3150 | Dgr = 30 | 500 to 30 | (6Wg - Rg + 5Wr - Rr)/2 | Sgr = 30; Ar ≠ Ag |
| 5Wr to 6 Wg | 3150 - 3180 | 30 to -30 | Sgr = 30 | (6Wg - Rg + 5Wr + Rr)/2 | Sgr = 30; Ar ≠ Ag |
| 6Wg to 6.5Wg | 3180 - 3445 | Dgr = -30 | 30 to 560 | (6Wg + Rg + 5Wr + Rr)/2 | Dgr = -30; Ar = Ag |
| 6.5Wg to 5.5Wr | 3445 - 3465 | -30 to -70 | Sgr = 560 | (7Wg - Rg + 5Wr + Rr)/2 | Sgr = 560; Ar ≠ Ag |
| 5.5Wr to 7Wg | 3465 - 3710 | Dgr = -70 | 560 to | (7Wg - Rg + 6Wr - Rr)/2 | Dgr = -70; Ar = Ag |

UNAMBIGUOUS RETARDANCE MEASUREMENT

CROSS REFERENCE TO RELATED APPLICATIONS

This application claims the benefit of U.S. Provisional Patent Application No. 62/055,140, entitled "UNAMBIGUOUS RETARDANCE MEASUREMENT" and filed on Sep. 25, 2014, which is hereby incorporated herein by reference.

TECHNICAL FIELD

This application relates to rapid and unambiguous measure of the retardance of optical samples such as polymers, plastics and crystals that may exhibit relatively high levels of retardance. This application incorporates by reference U.S. Pat. No. 6,985,227.

SUMMARY

Disclosed herein are representative embodiments of methods, apparatus, and systems for measuring the retardance of optical samples, such as polymers, plastics and crystals. The disclosed methods, apparatus, and systems should not be construed as limiting in any way. Instead, the present disclosure is directed toward all novel and nonobvious features and aspects of the various disclosed embodiments, alone and in various combinations and subcombinations with one another. Furthermore, any features or aspects of the disclosed embodiments can be used in various combinations and subcombinations with one another. For example, one or more method acts from one embodiment can be used with one or more method acts from another embodiment and vice versa. The disclosed methods, apparatus, and systems are not limited to any specific aspect or feature or combination thereof, nor do the disclosed embodiments require that any one or more specific advantages be present or problems be solved.

Many important optical materials exhibit birefringence. Birefringence means that different linear polarizations of light travel at different speeds through the material. These different polarizations are most often considered as two components of the polarized light, one being orthogonal to the other.

Birefringence is an intrinsic property of many optical materials, and may also be induced by external forces. Retardation or retardance represents the integrated effect of birefringence acting along the path of a light beam traversing the sample. If the incident light beam is linearly polarized, two orthogonal components of the polarized light will exit the sample with a phase difference, called the retardance. The fundamental unit of retardance is length, such as nanometers (nm). It is frequently convenient, however, to express retardance in units of phase angle (waves, radians, or degrees), which is proportional to the retardance (nm) divided by the wavelength of the light (nm). An "average" birefringence for a sample is sometimes computed by dividing the measured retardance magnitude by the thickness of the sample.

Oftentimes, the term "birefringence" is interchangeably used with, and carries the same meaning as, the term "retardance." Thus, unless stated otherwise, those terms are also interchangeably used below.

When measuring the retardance of a sample, only the phase difference between the two orthogonal polarizations of source light can be measured. The resulting effect is that the measurable retardance of a sample is always in the range zero to one wave at any discrete wavelength of source light, as follows.

$$\delta_A = m\pi + \delta_\lambda = 2\pi \frac{\Delta n L}{\lambda} \qquad \text{Eqn. 1}$$

In Equation 1, $\delta_A$ is the absolute retardance, m is an integer order, $\delta_\lambda$ is the measurable phase shift or measurable retardance, $\Delta n$ is the birefringence, L is the thickness of the sample, and $\lambda$ is the wavelength of source light. When the integer m is larger than 1, the absolute retardance is referred to as multiple order or multi-order retardance.

This invention is directed to methods of using the measured retardance, $\delta_\lambda$, at an arbitrary number of discrete wavelengths, $\lambda$, to robustly measure the absolute retardance, $\delta_A$ of an optical sample.

U.S. Pat. No. 7,385,696, hereby incorporated by reference, describes a method to measure multi-order retardation in samples with a known fast axis, such as stretched polymers. Among other things, this application also describes methods to measure multiple order retardation in samples with an arbitrary orientation of the fast axis.

In some example embodiments of the disclosed technology, a method for carrying out unambiguous retardance measurement of an optical sample includes directing, through a polarization state generator, source light with at least two different wavelengths; directing the light though the sample; directing the light though a polarization state analyzer; directing the light that emanates from the polarization state analyzer to an imaging device to thereby detect the intensity of the light and calculate a measurable retardance for each of the three wavelengths; and employing at least one of equations 5 and 8 (described further below) to determine the absolute retardance of the sample. In some example implementations, dispersion of light associated with the optical sample is accounted for. In further example implementations, wavelength fluctuations attributable to temperature variations of the source light is accounted for or prevented.

In other example embodiments, a method for measuring absolute retardance of an optical sample includes directing light with a plurality of wavelengths through a polarization state generator source, the optical sample, and a polarization state analyzer; detecting, at an imaging device, retardance measurement light emanating from the optical sample after also passing through the polarization state analyzer at the plurality of wavelengths; determining a measurement retardance associated with the detected retardance measurement light at each of the wavelengths; and determining an absolute retardance associated with the sample based on the measurement retardances determined at each of the wavelengths. In some example implementations, the optical sample has an arbitrary fast axis orientation with respect to the retardance measurement light directed to the optical sample. In further example implementations, the retardance measurement light extends over the optical sample so that the determined absolute retardance forms an absolute retardance image associated with a measurement area of the optical sample. Some examples of forming an absolute retardance image include directing the retardance measurement light to multiple positions of the sample and forming an absolute retardance image based on the absolute retardance determined at each of the positions with some absolute retardance images extending over multiple orders. In still further example implementations, the measuring of absolute retardance of an optical sample includes measuring an optical intensity of the received retardance measurement light wherein the measurement retardance at each of the wavelengths is determined based on the measured intensity.

In certain example implementations of the disclosed technology, the determining of an absolute retardance associated with an optical sample based on measurement retardances determined at a plurality of wavelengths includes: determining a plurality of expected retardances, each expected retardance corresponding to a wavelength of the plurality of wavelengths and being based on the measurement retardance determined for a selected wavelength of the plurality of wavelengths that is different from the wavelength corresponding to the expected retardance and being further based on one or more absolute retardance order estimates associated with an absolute retardance range; determining a plurality of error values associated with one or more wavelengths of the plurality of wavelengths by comparing the expected retardances with the measurement retardances; and determining the absolute retardance based on an absolute retardance order associated with a lowest error value of the plurality of error values for at least one of the plurality of wavelengths. Some examples also include averaging the absolute retardances determined for more than one wavelength of the plurality of wavelengths. In further examples, the expected retardances are scaled according to a dispersion aspect of the optical sample.

In further example implementations of the disclosed technology, the determining of an absolute retardance associated with an optical sample based on measurement retardances determined at a plurality of wavelengths includes: determining sum and difference retardances corresponding to at least two of the wavelengths based on a measurement retardance profile for the at least two wavelengths over an absolute retardance range; based on the sum and difference retardances, tabulating absolute retardance conditions over the absolute retardance range that include absolute retardance order values and measurement retardance sign associated with the at least two wavelengths; and determining the absolute retardance based on the determined measurement retardances and the tabulated absolute retardance conditions. In some examples, for measurement retardances corresponding to a sum and difference retardance near a retardance connecting region, determining the absolute retardance further includes determining values of absolute retardance for multiple orders of a multi-order range and associated with the measurement retardances determined for at least two of the wavelengths, and determining the absolute retardance based on the order having the least error between absolute retardance values.

Further, in some implementations, to determine absolute retardance, three or more wavelengths are used and the absolute retardance is further determined by averaging the absolute retardances determined from at least two pairs of the three or more wavelengths.

In certain example implementations of the disclosed technology, the determining of an absolute retardance associated with an optical sample based on measurement retardances determined at a plurality of wavelengths includes: determining values of absolute retardance for multiple orders of a multi-order range and associated with the measurement retardances determined for at least two of the wavelengths; and determining the absolute retardance based on the order having the least error between absolute retardance values. In some examples, absolute retardance is provided with an error margin associated with wavelength variability of the retardance measurement light. In further examples, determining an absolute retardance further includes determining a fast axis angle based on the measurement retardance at each wavelength, wherein determining the absolute retardance based on the order having the least error between retardance values includes distinguishing false absolute retardance values based on the determined fast axis angles.

Various systems for measuring retardance of an optical sample are also disclosed herein. One example system comprises a light source configured to generate light at a plurality of wavelengths; a polarization state generator configured to receive light from the light source and generate retardance measurement light having different polarization states; a sample positioned to have its retardance measured by the retardance measurement light; a polarization state analyzer configured to receive the retardance measurement light emanating from the sample; an imaging device configured to measure intensity of the retardance measurement light from the polarization state analyzer with different polarization states; and a retardance measurement system in communication with the imaging device and being programmed or configured to determine a measurement retardance associated with the detected measurement light at each of the wavelengths and to determine an absolute retardance associated with the sample based on the measurement retardances determined at each of the wavelengths.

Other advantages and features of the present invention will become clear upon study of the following portion of this specification, claims, and drawings.

BRIEF DESCRIPTION OF DRAWINGS

FIGS. 5A-B show a tabulation including the sum and difference data of FIG. 4 for discrete ranges of actual multi-order retardation levels as well as associated conditions of that data that permit unambiguous determination of the actual multi-order retardation level for given measured retardation levels.

DETAILED DESCRIPTION

Figure 1:
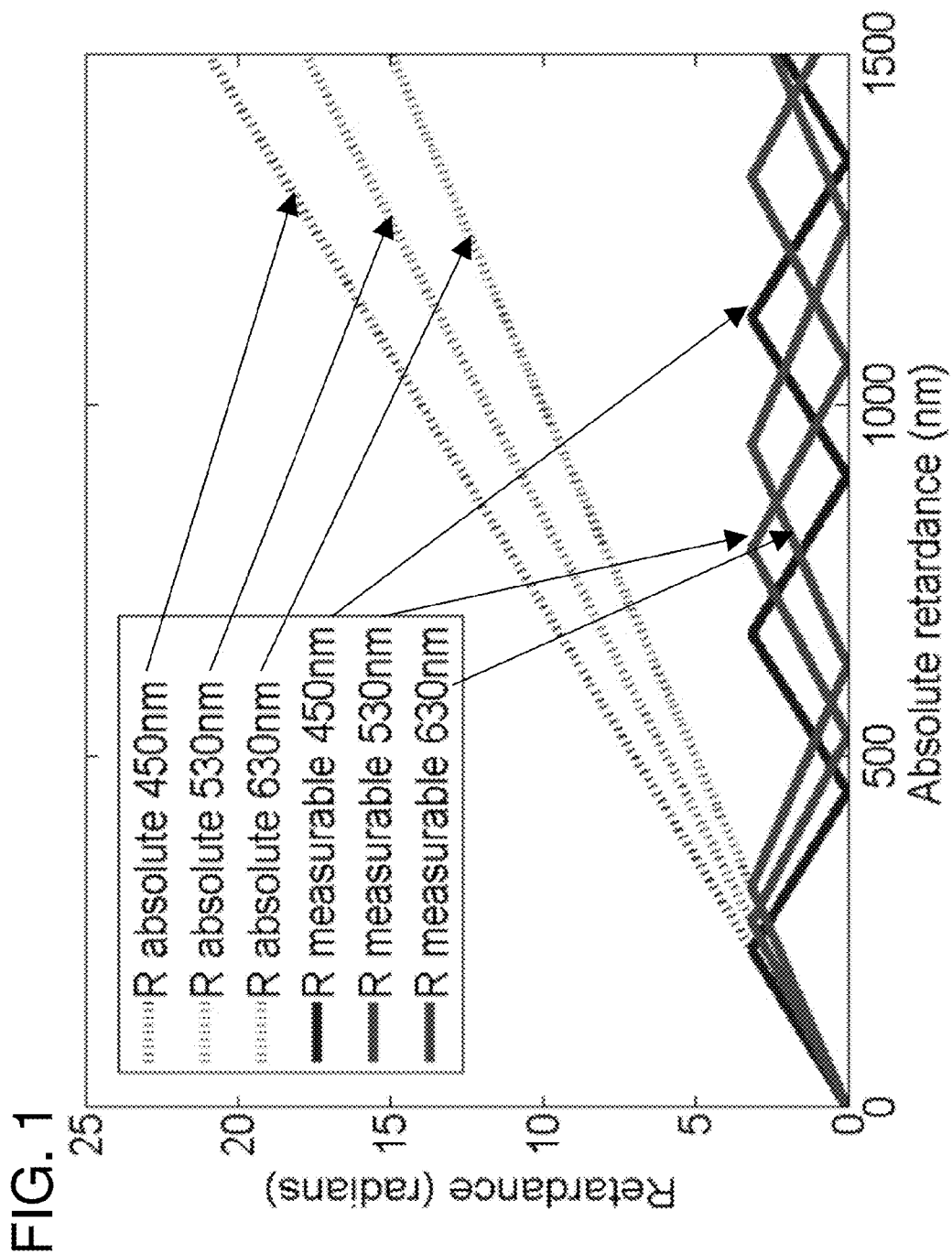
FIG. 1 is a graph showing the absolute retardance level in nanometers versus the measurable and absolute retardance in radians at three different wavelengths of source light.

Example Method I: Using Measured Retardance, $\delta_\lambda$, at an Arbitrary Number of Discrete Wavelengths, $\lambda$, to Robustly Measure Absolute, Multi-Order Retardance $\delta_A$ of an Optical Sample FIG. 1 illustrates the principle underlying the present invention by mapping the retardance in nanometers versus the absolute and measurable retardance at three different source light wavelengths.

As described more below, the present invention provides for unambiguous retardance measurement by, among other things, precisely establishing the correct integer order m. The approach is to "unwrap" the measured retardance into the absolute retardance using multiple wavelength measurements. This method is applicable to single point measurement of multiple wavelengths, and is thus equally valid for either imaging or point based measurement systems.

Some prior phase unwrapping techniques rely solely upon the identification of the peak regions and their gradients. These methods require robust treatment of spatial information and are prone to errors. The multi-wavelength method of the present invention, on the other hand, is based upon the information for a single point and less prone to error induced by samples with large spatial diversity.

The ability to unwrap the retardance over numerous orders is particularly important to imaging (over an area, as opposed to point based systems) where most samples are multi-order polymers, plastics, and crystals. Point based measurement systems generally show extremely high sensitivity and are geared toward the measurement of low retardance levels, far less than a single order. Imaging systems tend to have lower sensitivity, but can quickly measure whole fields and large areas. The orders of retardance may span thousands of nanometers, and this order diversity makes phase unwrapping particularly important to birefringence imaging.

Figure 2:
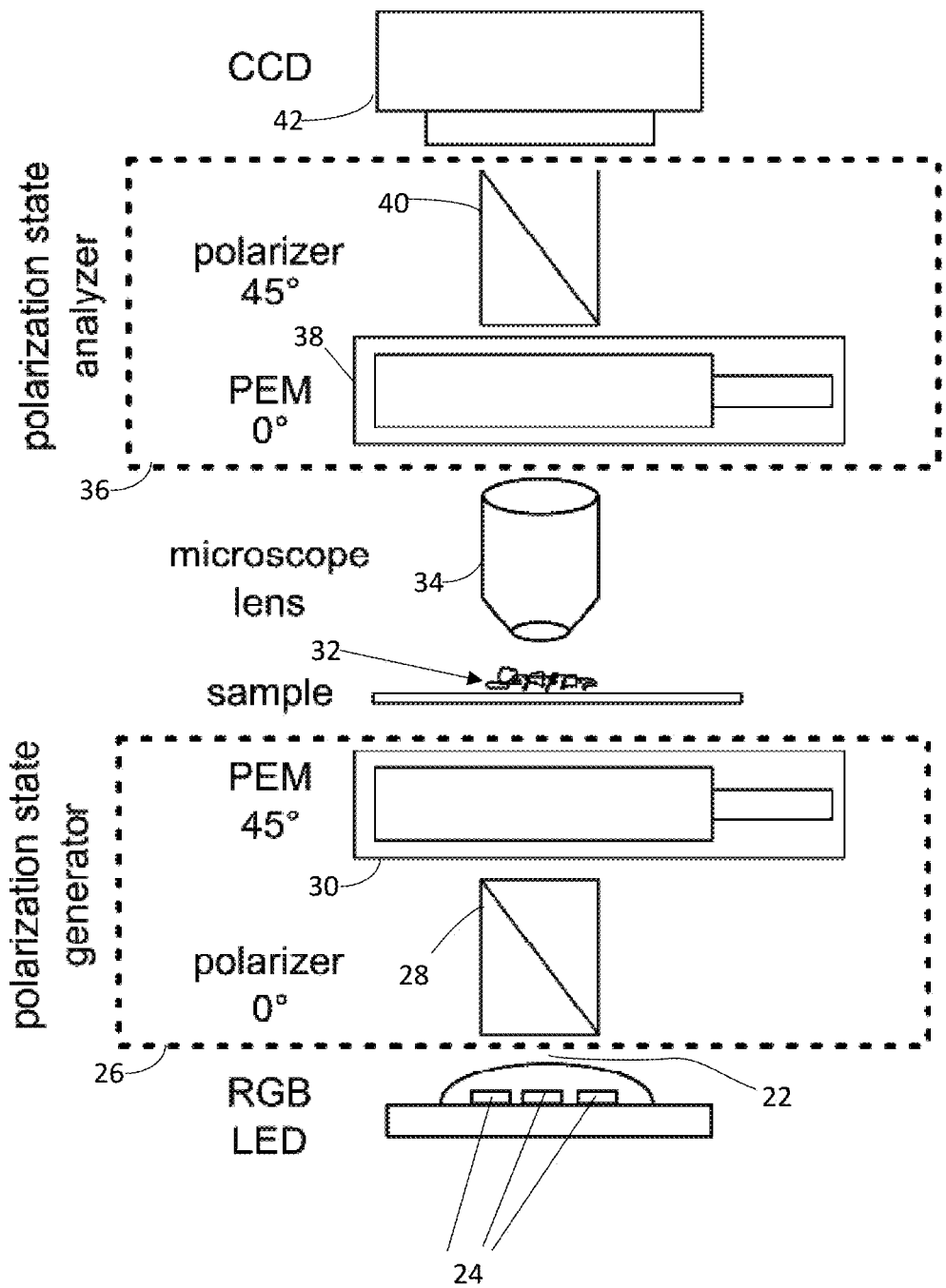
FIG. 2 is block diagram of one embodiment of a system for carrying out the method of the present invention.

FIG. 2 illustrates one embodiment of system 20 for carrying out method of the present invention. The multiple wavelengths of the source light 22 are generated by light emitting diodes (LEDs) 24 with three different wavelengths, in this case, red (630 nm), blue (450 nm) and green (530 nm).

The light emanating from these LEDs 24 passes through a polarization state generator 26 consisting of a linear polarizer 28 and a polarization modulating element such as a photoelastic modulator 30. The light then passes through the sample 32, and into the imaging optics, which may include, for example, a microscope lens 34. From here, the light enters a polarization state analyzer 36, consisting of a polarization modulating element 38 and a linear polarizer 40. The light then is imaged onto a CCD-type camera 42 to measure the intensity. From the images of intensity with different polarization states of the light, the retardance can be measured. Specifically, the measured retardance at the three wavelengths is treated with the following algorithm to measure the absolute retardance, as described next. The algorithm may be, for example, embodied as software or firmware instructions carried out by a digital computer. For instance, any of the disclosed retardance measurement techniques can be performed by a computer or other computing hardware (e.g., an ASIC or FPGA) that is part of a retardance measurement system. The retardance measurement system can be connected to or otherwise in communication with the imaging device (e.g., the CCD) and be programmed or configured to receive imaging data from the imaging device and perform the desired retardance measurement computations (e.g., any of the retardance measurement techniques disclosed herein). The computer can be a computer system comprising one or more processors (processing devices) and tangible, non-transitory computer-readable media (e.g., one or more optical media discs, volatile memory devices (such as DRAM or SRAM), or nonvolatile memory or storage devices (such as hard drives, NVRAM, and solid state drives (e.g., Flash drives)). The one or more processors can execute computer-executable instructions stored on one or more of the tangible, non-transitory computer-readable media, and thereby perform any of the disclosed techniques. For instance, software for performing any of the disclosed embodiments can be stored on the one or more volatile, non-transitory computer-readable media as computer-executable instructions, which when executed by the one or more processors, cause the one or more processors to perform any of the disclosed retardance measurement techniques. The results of the computations can be stored (e.g., in a suitable data structure or lookup table) in the one or more tangible, non-transitory computer-readable storage media and/or can also be output to the user, for example, by displaying, on a display device, point or image-based absolute retardances with a graphical user interface. In particular examples, image based mappings of multi-order absolute retardances across an optical sample (e.g., as measured with techniques disclosed herein) are displayed on a display device.

Figure 8:
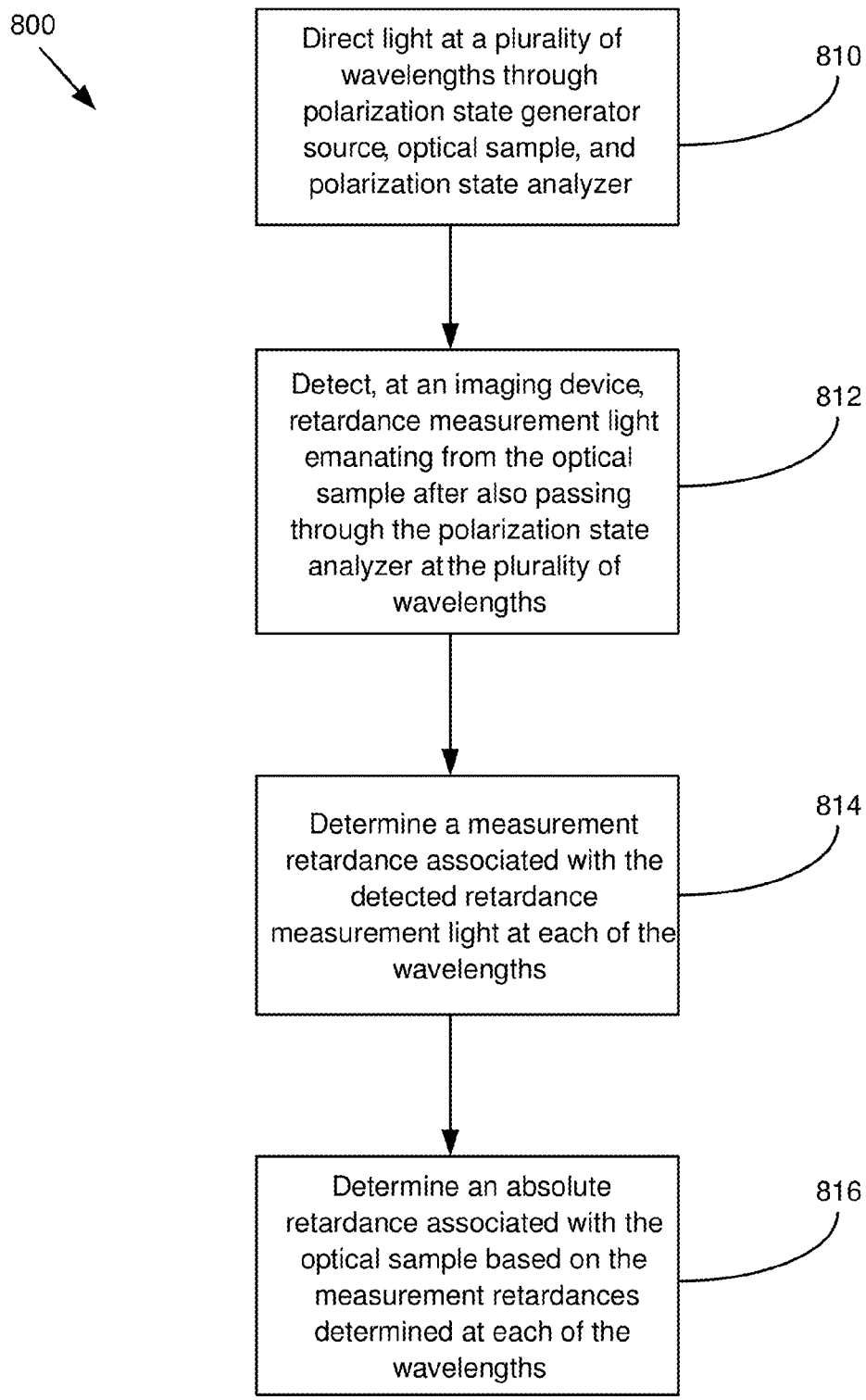
FIG. 8-11 are flowcharts of example methods for determining absolute retardance in accord with various aspects of the present invention.

In a general example for measuring absolute retardance, reference is made to FIG. 8 and method example 800. At 810, light is directed at a plurality of wavelengths (simultaneously or sequentially) through a polarization state generator source, an optical sample, and a polarization state analyzer. At 812, an imaging device detects retardance measurement light emanating from the optical sample after also passing through the polarization state analyzer at the plurality of wavelengths. At 814, a measurement retardance associated with the detected retardance measurement light is determined at each of the wavelengths. At 816, an absolute retardance is determined for the optical sample that is based on the measurement retardances determined at each of the wavelengths. For instance, any of the example techniques for determining absolute retardance disclosed herein (e.g., Examples Methods 1, 2, 3, or 4) can be used to determine the absolute retardance based on the measured retardances at each of the wavelengths.

The measurable retardance, $\delta_\lambda$, is collected at a number of discrete wavelengths, $\lambda_1, \lambda_2 \ldots \lambda_N$. The exact birefringence at each wavelength is slightly different, but for an adequately small range of wavelengths, the birefringence, $\Delta n$, can be considered constant. This approximation allows for the measurement of the retardance at multiple wavelengths and the absolute determination of the order.

The measured retardance, $\delta_k$, at a single wavelength, $\lambda_k$, is used to calculate the expected retardances, $\delta_{g2} \ldots \delta_{gN}$, at every other measured wavelength as shown below.

$$\delta_{gn} = cyc\left[(m_g\pi + \delta_k)\frac{\lambda_k}{\lambda_n}\right] \quad \text{Eqn. 2}$$

In Equation 2, above, the function cyc is a function that enforces the cyclical behavior such as a remainder or $\cos^{-1}[\cos f]$ function. The guessed order, $m_g$, is taken to cover the entire likely range of order values. For example, based on an absolute retardance range, the largest order associated with that range may be used to determine an expected retardance and expected retardances corresponding to smaller orders may be determined subsequently. However, it will be appreciated that other sequences of expected retardance determination may be used, including parallel determinations. The guessed retardances, $\delta_{gn}$, at each wavelength, $\lambda_g$, are then used to calculate an error value against each measured retardance, $\delta_{\lambda n}$, at the different wavelengths, $\lambda_n$, as shown in Equation 3, below.

$$\epsilon_g = \sqrt{\Sigma_{n \neq k}^N (\delta_{\lambda n} - \delta_{gn})} \quad \text{Eqn. 3}$$

The determined correct order is the guessed order, $m_g$, that has the lowest error value. The measured retardance, $\delta_k$, and wavelength, $\lambda_k$, are then cycled through all the measured wavelengths. Thereby, at each wavelength, there is the determined correct order, $m_i$. These wavelengths and orders are then used to calculate the determined absolute retardance, $\delta_{Ai}$, at each wavelength as shown in Equation 4, below.

$$\delta_{Ai} = m_i \pi + \delta_i \qquad \text{Eqn. 4}$$

The average of the determined absolute retardance for all wavelengths is then taken to be the measured absolute retardance. The advantage of this method is that the use of a sufficient number of wavelengths allows for the elimination of bad measurements, and the correct order is selected even when the error between two guessed orders is nearly identical at any single wavelength.

In highly dispersive media (optical samples) or over a wide spectral range, the above-noted assumption of invariant birefringence, $\Delta n$, may not be appropriate. In this case, the guessed retardance equation can be altered to take into account dispersion as shown below.

$$\delta_{gn} = cyc\left[D_{k\to n}(m_g\pi + \delta_k)\frac{\lambda_k}{\lambda_n}\right] \qquad \text{Eqn. 5}$$

In Equation 5, $D_{k\to n}$ is a scaling factor equal to the ratio of retardance at each wavelength as shown below:

$$D_{k\to n} = \frac{\Delta n(\lambda_n)}{\Delta n(\lambda_n)} \qquad \text{Eqn. 6}$$

In Equation 6, $\Delta n(\lambda)$ is a function that describes the birefringence dispersion of the material. For most commonly examined substances across the entire visible spectrum, this ratio is on the order of unity±0.7%, and hence, is commonly neglected. The above averaging scheme also tends to cancel out this birefringence variability because the determined absolute retardance, $\delta_A$, is calculated using both extremes of the wavelength range and averaged.

When using LEDs as the light source, care must be taken to account for or avoid the central wavelength fluctuations of an LED with temperature. As the temperature of the LED junction rises, the wavelength of the LED shifts to higher wavelength. This shift is typically on the order of 4-8 nm over the likely temperature range of room temperature to 120° C. This would mean a measurable retardance shift of around 1-2%. The change in wavelength can be accounted for by measuring the junction temperature or using Peltier temperature control. The latter is preferable as it allows the LED to be maintained below 0° C. where the light flux can be double or triple compared to higher temperatures.

Figure 9:
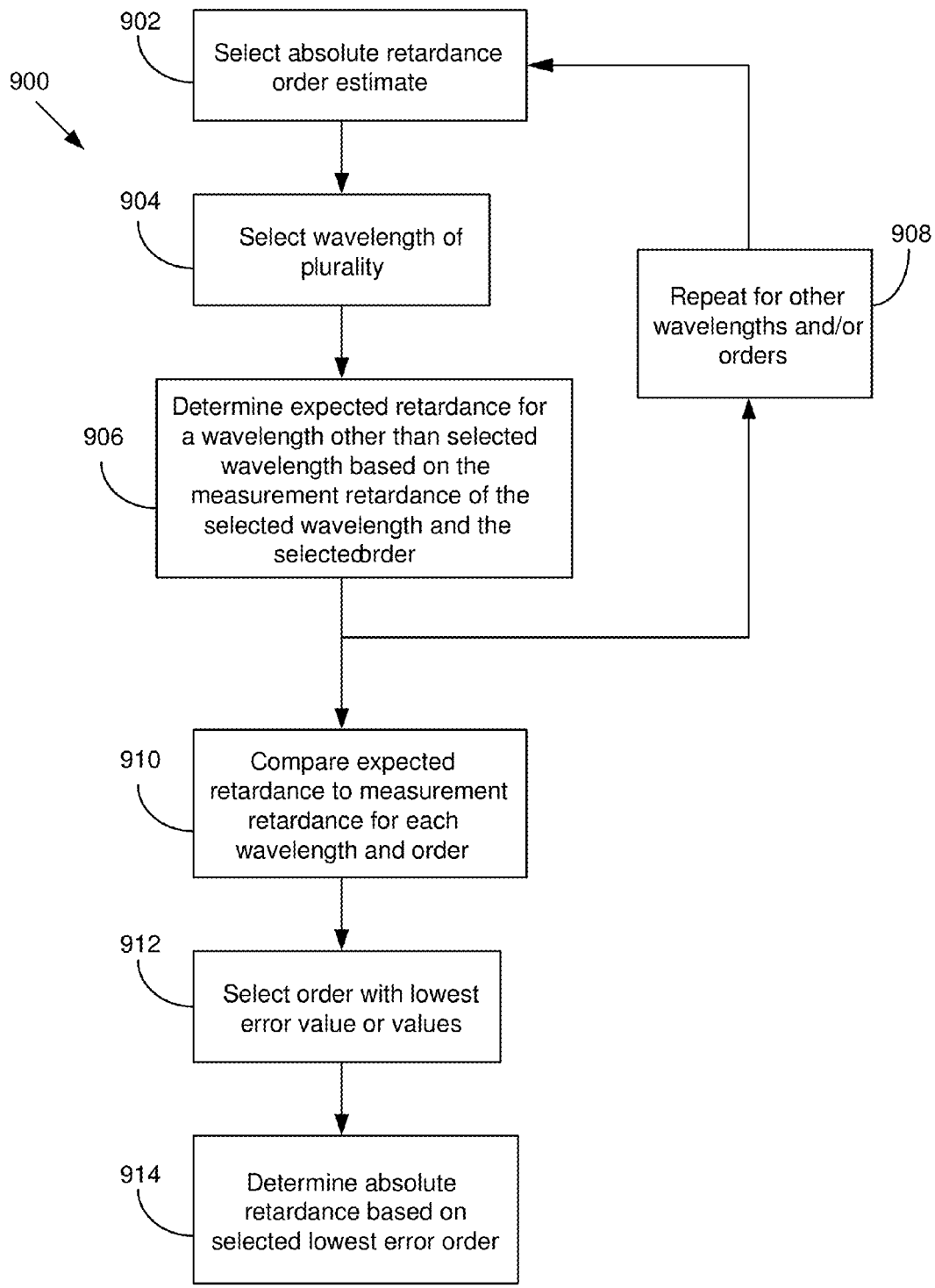

An example method 900 for determining absolute retardance using Method Example I and general example 800 is depicted in FIG. 9. At 902 and 904, an absolute retardance order estimate and a wavelength of the plurality of wavelengths are selected. At 906, an expected retardance is determined for a wavelength other than the wavelength selected at 904, the expected retardance being based on the measurement retardance for the wavelength selected at 904 and the order estimated at 902. The selection of absolute retardance order and wavelength and determination of a corresponding expected retardance is repeated for other wavelengths and orders at 908 until a sufficient number of expected retardances are determined. In typical examples, for each wavelength expected retardances are determined for each order in the absolute retardance range. At 910, the plurality of expected retardances that have been determined at 906 are compared to measurement retardances. At 912, an absolute retardance order is selected that is associated with one or more lowest error values. At 914, the absolute retardance is determined based on the selected lowest order.

Example Method II: Multi-Order, Absolute Retardation Measurement Using Two Wavelengths This method is used to measure multiple order retardation in samples having an arbitrary orientation of the fast axis.

Figure 3:
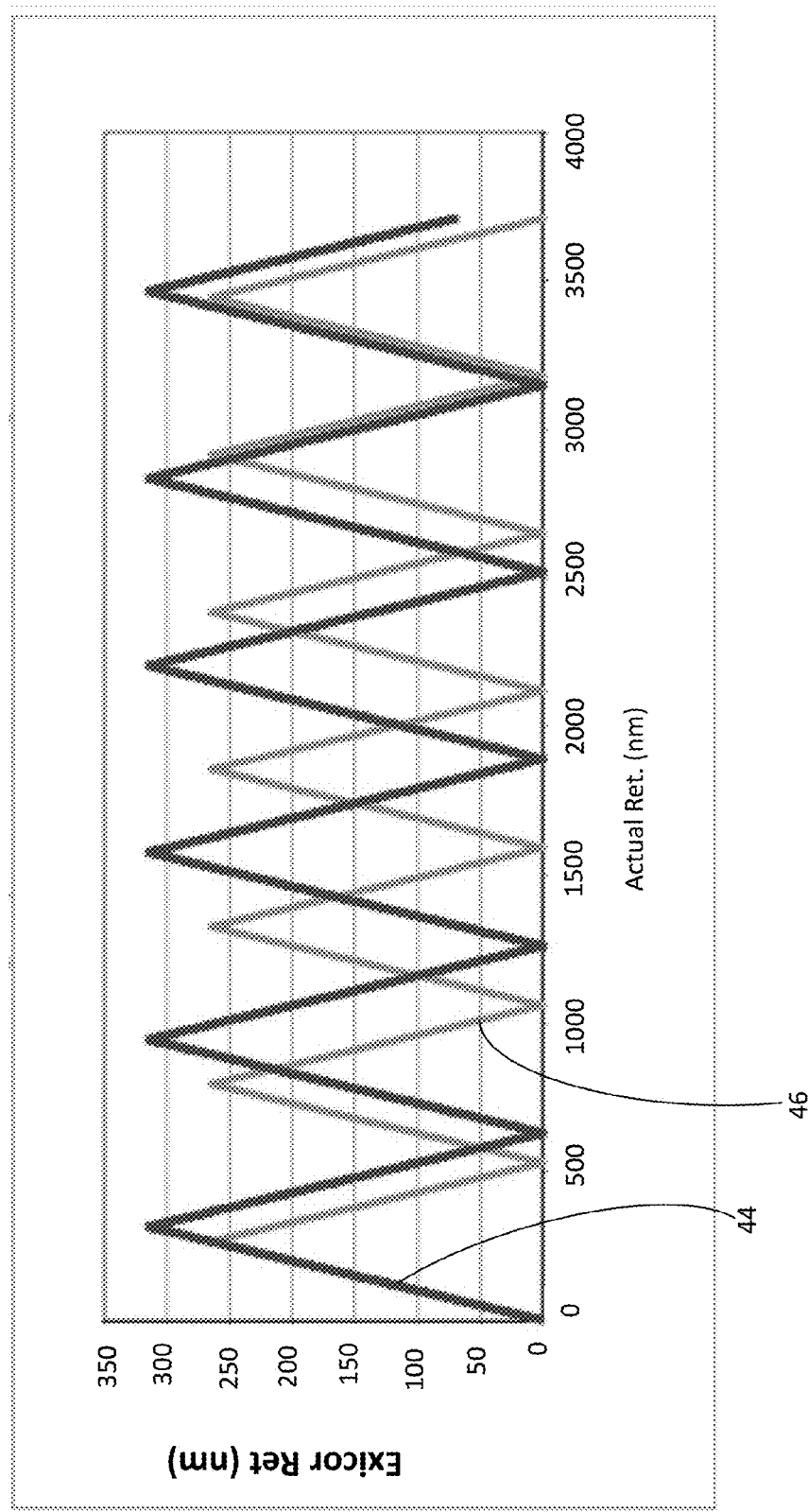
FIG. 3 is a graph depicting retardation curves for a sample that is measured at two different wavelengths in accord with one aspect of the present invention.

FIG. 3 depicts actual retardation data measured at two different wavelengths by a birefringence measurement system such as one marketed under the trademark, Exicor, manufacture by Hinds Instruments of Hillsboro, Oreg. and as described in pertinent part in U.S. Pat. Nos. 6,985,227 and 7,385,696 (hereafter the system is occasionally referred to as the "Exicor Instrument"). The Y-axis represents the measured ("Exicor") retardance in nanometers. The X-axis represents values of actual retardation in nanometers (nm).

In FIG. 3, the red line 44 represents measured results from a red light source having a wavelength of 630 nm; the green line 46 represents measured results from a green light source with a wavelength of 530 nm. As described in U.S. Pat. Nos. 6,985,227 and 7,385,696, the Exicor instrument provides retardation data from 0 to half of the wavelength used for each source wavelength. When the actual retardation values are beyond half of the measured wavelength, they either "fold" back or repeat.

Put another way, when two different wavelengths are used for the retardation measurement, the possible measurements that are based on these wavelengths are illustrated in the graph of FIG. 3 as lines 44 and 46. That is, FIG. 3 shows several retardation measurements of the system in which two light sources, operating at wavelengths of 630 nm (red line 44) and 530 nm (green line 46) are employed. The graph of FIG. 3 thus illustrates the relationship between the (several) measured retardation values at 630 nm and 530 nm and the actual retardation in the range from 0 to nearly 3,700 nm. For any given sample, the actual retardation of the sample will correspond to only one of the several, measured retardation values. In one case, an approach for determining the actual retardation is discussed next.

The retardation magnitude and angle of fast axis of a sample can be expressed as:

$$\rho = \frac{1}{2}\tan^{-1}\left[\frac{R_2}{R_1}\right] \text{ or} \qquad \text{Eqn. (7.1)}$$

$$\rho = \frac{1}{2}ctg^{-1}\left[\frac{R_1}{R_2}\right]$$

$$\delta = \tan^{-1}\left(\sqrt{\left(\frac{R_1}{R_3}\right)^2 + \left(\frac{R_2}{R_3}\right)^2}\right) \text{ or} \qquad \text{Eqn. (7.2)}$$

$$\delta = \cos^{-1} R_3$$

where $\delta$, represented in radians, is a scalar. When measured at a specific wavelength (e.g., 630 nm), $\delta$ can be converted to retardation in "nm" ($\delta_{nm} = \delta_{rad} \cdot 630/(2\pi)$).

Using the sign information of the raw data, equations (7.1) and (7.2) lead to unambiguous determination for both the magnitude and angle of fast axis of linear retardation in the range of 0-$\pi$ (half wave).

When the actual retardation is between $\pi$ and $2\pi$, the present embodiment will report a retardation value between 0 and $\pi$ and an angle of fast axis that is shifted by 90°.

Figure 4:
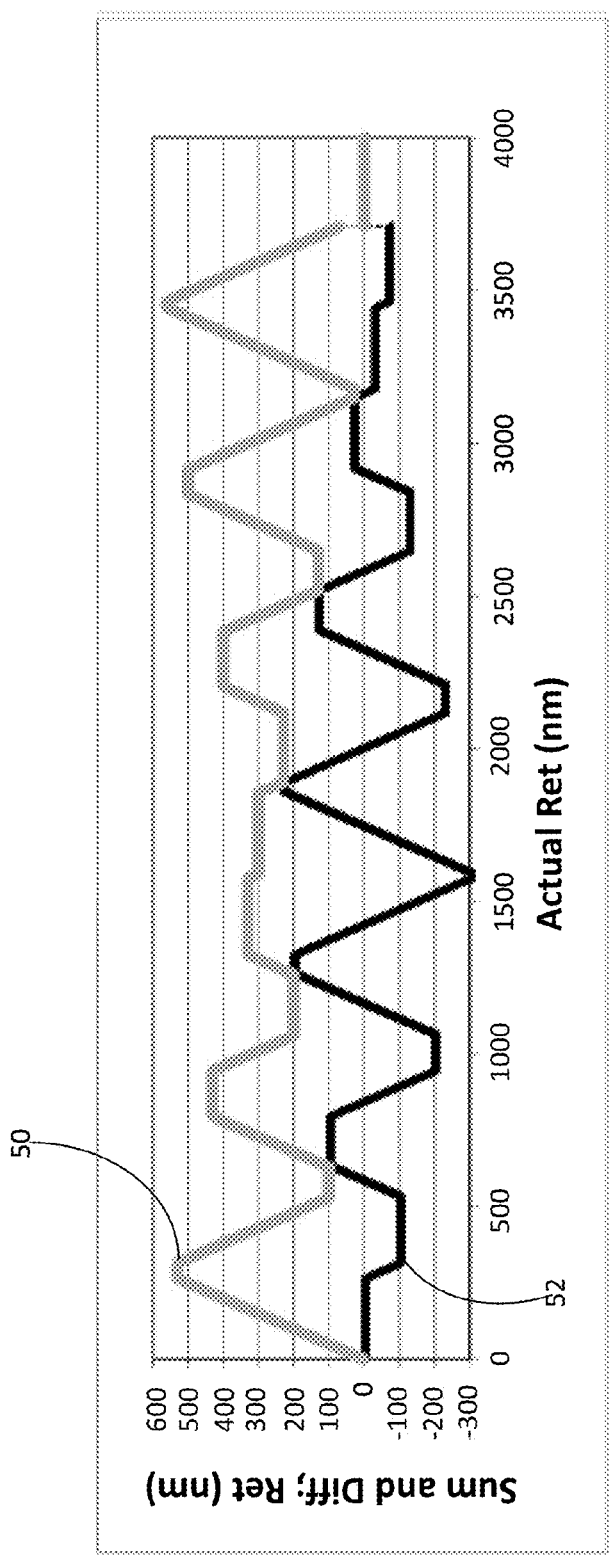
FIG. 4 is a graph depicting the sum and differences of the measured retardation data at the two wavelengths as depicted in FIG. 3.

This method next requires determination of the sum and difference of the measured retardation data at the two different wavelengths. In this regard, FIG. 4 depicts via line 50 the sum of the two measured retardance values (that is, for each wavelength) read on the Y-axis, relative to the actual retardance, read on the X-axis. Line 52 of FIG. 4 depicts the difference of the two measured retardance values (that is, for each wavelength) read on the Y-axis, relative to the actual retardance, read on the X-axis. It is noted that when the sum line 50 is flat, the difference line 52 is changing; when the difference is flat, the sum is changing. Moreover, there is always a flat segment in either the sum or difference curves for the entire range of retardation interested (0-3700 in this example).

With the foregoing in mind, the next step of this method is to establish a tabulation based on the following equation for calculating the actual value of the multi-order retardation of the optical sensor:

$$Ret(mo)=(mWg+/-Rg+nWr+/-Rr)/2 \qquad \text{Eqn. 8.0}$$

Where, in this example, Ret(mo) is the multi-order, actual retardation value; Wg is the wavelength for the green light (530 nm); Wr is the wavelength for the red light (630 nm); Rg is the retardation value measured at the green wavelength; Rr is the retardation value measured at the red wavelength; and m and n are positive integers.

Depending on the measured values at green and red wavelengths, specific conditions determine the values of m and n, as well as whether either a "+" sign or a "−" sign is positioned in front Rg and Rr in equation 8.0. A set of these conditions are tabulated in Table I that appears as FIGS. 5A-5B. In that table, the data in column (2), "Dgr", represents the difference between the retardation value measured at the green wavelength (Rg) and the retardation value measured at the red wavelength (Rr), or Dgr=Rg-Rr. Similarly, the data "Sgr" in column (3) of Table I (FIGS. 5A-B) represents the sum of the retardation value measured at the green wavelength (Rg) and the retardation value measured at the red wavelength (Rr), or Sgr=Rg+Rr.

Upon review of the table, it will be appreciated that the relationship between the each row of data in columns (2) and (3) (that is, the difference and sum data just discussed) corresponds to particular, discrete ranges of actual retardation values from 0 nm to the maximum, which in this example is about 3700 nm. Thus, the analysis of the sum and difference curves of FIG. 4, as tabulated in FIGS. 5A-B, permit determination of the actual, multi-order retardation measure without ambiguity, and the calculation for making that determination is provided in column (4) of the table.

For example, in an instance where the difference Dgr between the retardation value measured at the green wavelength Rg and the retardation value measured at the red wavelength Rr happens to be −200, and the sum Sgr of the retardation value measured at the green wavelength and the retardation value measured at the red wavelength Rr is between 430 to 200 nm, the table of FIGS. 5A-B reveals (in the seventh row of data) that the actual retardation value (Ret(mo)) will occur in the range of 945 to 1060 nm (see columns (1a) and (1b)), and in particular that actual value will be (see column (4)):

$$Ret(mo)=(2Wg-Rg+2Wr-Rr)/2 \qquad \text{Eqn. 9.0}$$

It is noteworthy that there is practically no theoretical upper limit for multiple order retardation values. However, in practice, the accuracy and noise level of the instrument will restrict the upper limit of the multi-order retardation values that one can determine. In the example above, the retardation values were limited to below 3700 nm.

The final step for this method involves the determination of the angle of the fast axis. This step includes the substep of calculating the remainder value (Rrmn) for the red wavelength as the fraction of the determined actual retardation, Ret(mo), over the wavelength (630) of the red light, or Rrmd=Ret(mo)/630; and calculating the remainder value (Grmn) for the green wavelength as the determined actual retardation, Ret(mo), over the wavelength (530) of the green light, or Grmd=Ret(mo)/530.

For the determined remainder values, application of those values to the following set of conditions will yield the direction of the fast axis:

If Rrmd < 10 or |Rrmd − 315| < 10 is true:
    then, if Grmd < 265, Fast axis = measured fast axis at green; or
    if Grmd > 265, Fast axis = 90° + measured fast axis.
Otherwise:
    for Rrmd < 315, Fast axis = measured fast axis at red; and
    for Rrmd > 315, Fast axis = 90° + measured fast axis.

Figure 10:
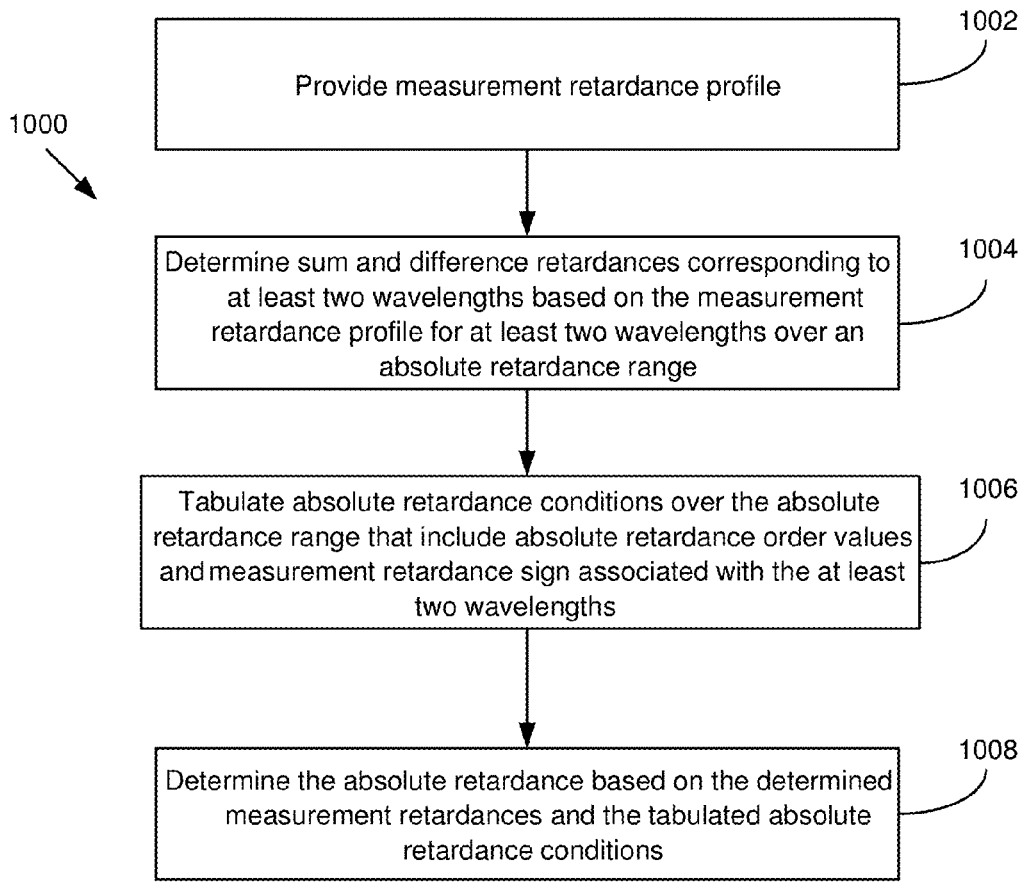

An example method 1000 for determining absolute retardance using Method Example II and general example 800 is depicted in FIG. 10. At 1002, a measurement retardance profile is provided. At 1004, over a selected absolute retardance range, sum and difference retardances are determined that correspond to at least two wavelengths based on the measurement retardance profile from 1002 for the at least two wavelengths. At 1006, absolute retardance conditions over the selected absolute retardance range are tabulated. The absolute retardance conditions can include absolute retardance order values and measurement retardance sign (e.g., positive or negative) associated with the at least two wavelengths. At 1008, the absolute retardance is determined based on previously determined measurement retardances and the tabulated absolute retardance conditions.

Figure 6:
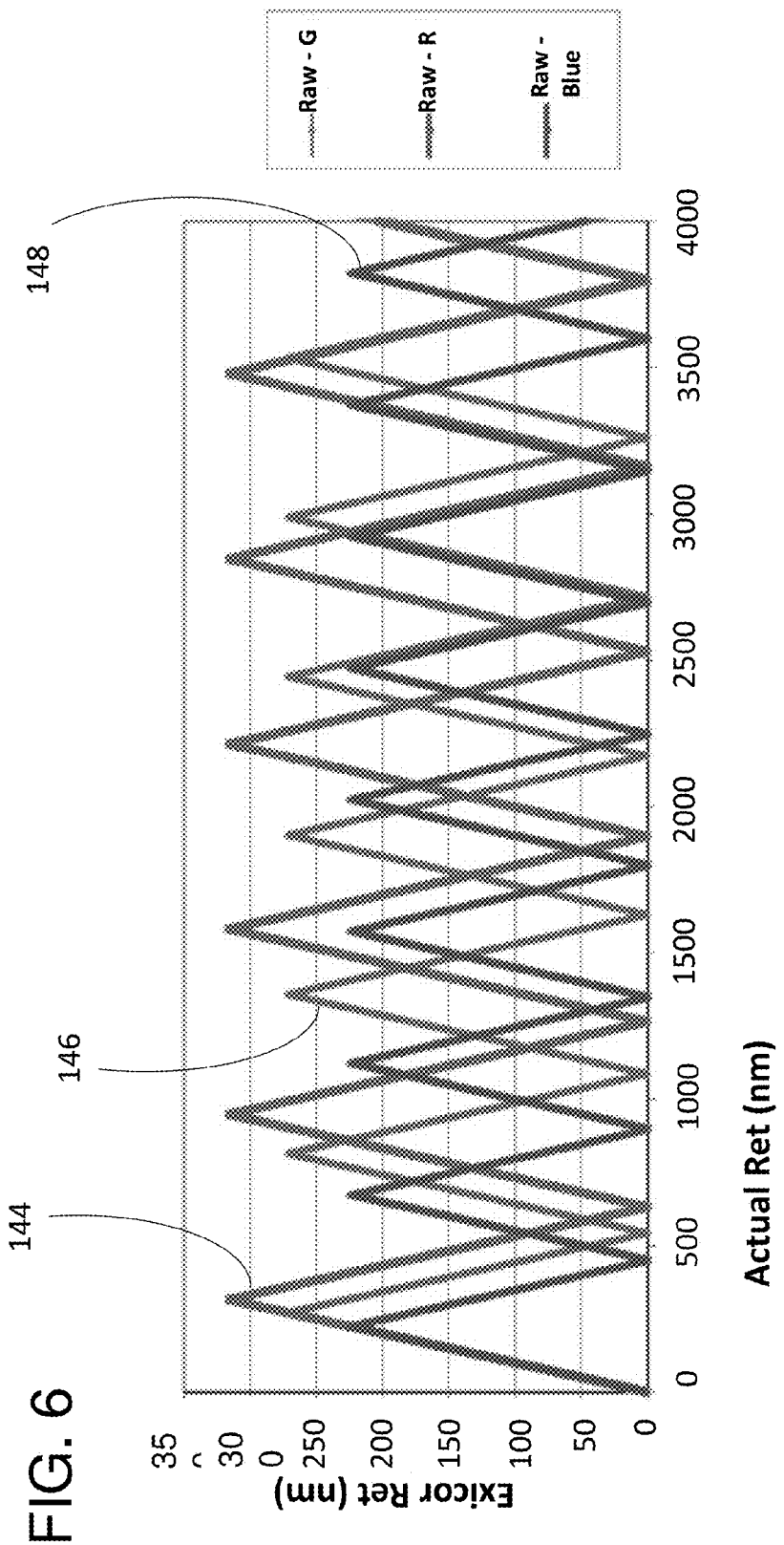
FIG. 6 is a graph depicting retardation curves for a sample that is measured at three different wavelengths in accord with another aspect of the present invention.

Example Method III: Multi-Order, Absolute Retardation Measurement Using Three or More Wavelengths FIG. 6 is similar to FIG. 3 and depicts actual retardation data measured at three different wavelengths by a birefringence measurement system such as the Exicor Instrument, as described in pertinent part in U.S. Pat. Nos. 6,985,227 and 7,385,696.

In FIG. 6, the red line 144 represents measured results from a red wavelength of 630 nm; the green line 146 represents measured results from a green wavelength of 530 nm, and the blue line 148 represents measured results from a blue wavelength at 458 nm.

With three measuring wavelengths, there are three pairs of data one can use to determine multi-order retardation values—the green-red pair as used above in Method II, the green-blue pair and the red-blue pair. Each wavelength pair will have its own set of conditions to calculate multiple order retardation. Using the average of them will improve measurement accuracy.

Figure 7:
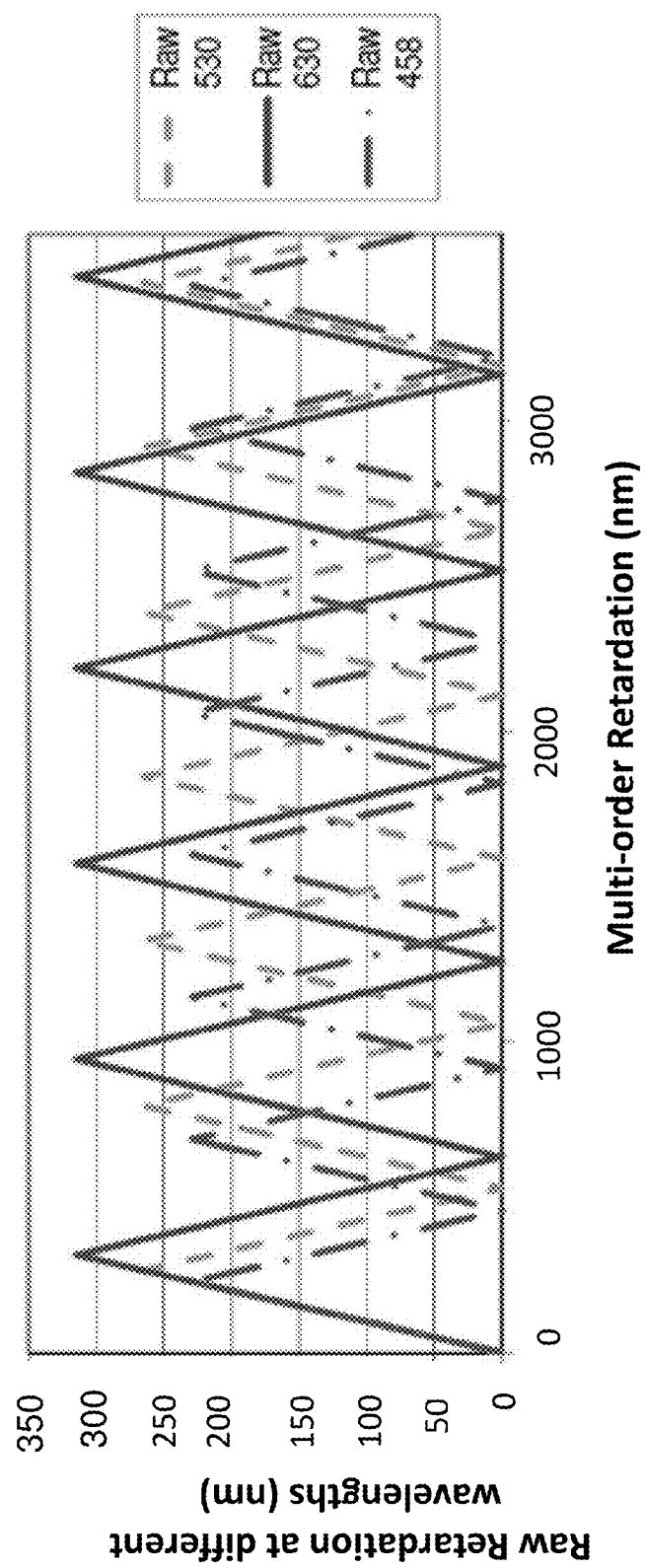
FIG. 7 is a graph depicting retardation curves for a sample that is measured at three different wavelengths in accord with yet another aspect of the present invention

Example Method IV: Multi-Order, Absolute Retardation Measurement Using Mathematic Fitting FIG. 7 is similar to FIG. 6 and depicts simulated retardation data measured at three different wavelengths by the Exicor Instrument birefringence measurement system. As before, the Y-axis represents the measured (simulated) retardance in nanometers. The X-axis represents values of actual retardation in nanometers (nm).

In FIG. 7, the red line 244 represents measured results from a red wavelength of 630 nm; the green line 246 represents measured results from a green wavelength of 530 nm, and the blue line 248 represents measured results from a blue wavelength at 458 nm. In accordance with this method, the actual multi-order retardation can also be calculated from the raw data measured at multiple wavelengths using mathematic fitting. For theoretical analysis purpose, the FIG. 7 shows a simulation of the measured raw retardation data at red, green and blue wavelengths versus the multi-order retardation.

The following notations are used in explaining the method:
Three wavelengths: Wr, Wg, and Wb
Rr: Raw retardation value measured at a red wavelength;
Rg: Raw retardation value measured at a green wavelength;
Rb: Raw retardation value measured at a blue wavelength;
Ar: Raw fast axis angle value measured at a red wavelength;
Ag: Raw fast axis angle value measured at a green wavelength;
Ab: Raw fast axis angle value measured at a blue wavelength;
Order of retardation at a particular wavelength: Nr, Ng, and Nb (positive integers).

As seen in FIG. 7, any raw retardation value measured at a particular wavelength (any point on the vertical axis) corresponds to a number of possible multi-order retardation values. Quantitatively, an Rr value could correspond to any of the multi-order retardation values that can be represented as either (Nr·Wr−Rr) or ((Nr−1)·Wr+Rr). Similarly, a Rg value could correspond to any of the multi-order retardation values that can be represented as either (Ng·Wg−Rg) or ((Ng−1)·Wg+Rg); the Rb value could correspond to any of the multi-order retardation values that can be represented as either (Nb·Wb−Rb) or ((Nb−1)·Wb+Rb).

The present Method IV is carried out as follows:
Step 1. Based on the raw value of Rr, Rg, and Rb, calculate all possible values of multi-order retardation values at different N values.
a. MORr=(Nr·Wr−Rr) and ((Nr−1)·Wr+Rr)
b. MORg=(Ng·Wg−Rg) and ((Ng−1)·Wg+Rg)
c. MORb=(Nb·Wb−Rb) and ((Nb−1)·Wb+Rb)

The range of N, thus the range of multi-order retardation values, is extremely large theoretically. In practice, measurement errors at different wavelengths limit this range significantly. Using 1 to 10 for N in the example demonstrates the method:
Example: Simulated raw data Rr=240 nm; Rg=40 nm; Rb=104 nm (occurring as illustrated by the vertical line 250 in FIG. 7

All possible values of multi-order retardation at three different wavelengths and at different N values from 1 to 10 appear in the following Table II:

| | MORr Wr = 630 nm; Rr = 240 nm | | MORg Wg = 530 nm; Rg = 40 nm | | MORb Wb = 458 nm; Rb = 104 nm | |
|---|---|---|---|---|---|---|
| N | NrWr − Rr | (Nr − 1) · Wr + Rr | Ng · Wg − Rg | (Ng − 1) · Wg + Rg | Nb · Wb − Rb | (Nb − 1) · Wb + Rb |
| 1 | 390 | 240 | 490 | 40 | 354 | 104 |
| 2 | 1020 | 870 | 1020 | 570 | 812 | 562 |
| 3 | 1650 | 1500 | 1550 | 1100 | 1270 | 1020 |
| 4 | 2280 | 2130 | 2080 | 1630 | 1728 | 1478 |
| 5 | 2910 | 2760 | 2610 | 2160 | 2186 | 1936 |
| 6 | 3540 | 3390 | 3140 | 2690 | 2644 | 2394 |
| 7 | 4170 | 4020 | 3670 | 3220 | 3102 | 2852 |
| 8 | 4800 | 4650 | 4200 | 3750 | 3560 | 3310 |
| 9 | 5430 | 5280 | 4730 | 4280 | 4018 | 3768 |
| 10 | 6060 | 5910 | 5260 | 4810 | 4476 | 4226 |

Step 2. Referring to the data of Table II, the calculated MORr, MORg, and MORb values are compared. There is only one value that is the same at all three wavelengths and that value is the true multi-order retardation. In this example, 20 possible values at each wavelength for N from 1 to 10 were calculated. The value "1020 nm" is the only one value that is the same for all three wavelengths. Therefore, the true multi-order retardation value is 1020 nm.

There is no other value in the above table that is the same for all three wavelengths. The next closest set of values are MORr=1500 nm; MORg=1550 nm; and MORb=1478 nm, where the largest difference between the MORr, MORg and MORb values is 72 nm. Another set of values are MORr=4020 nm; MORg=4200 nm; and MORb=4018 nm where MORr is very close to MORb but MORg is 182 nm higher than MORb.

Step 3. When the range is significantly expanded beyond N=10, there may be cases where all three MORr, MORg, and MORb values approach the same value. More importantly in practice, there are experimental errors in all measurements. When the multi-order retardation is determined using "the same at all three wavelengths", "the same value" is not an exact value anymore. It becomes a range of values and the range depends on the experimental errors. For example, as shown in the following Table III, the MORr, MORg, and MORb values all contain "3098". Therefore, true multi-order retardation value is 3098 nm.

| | MORr<br>Wr = 630 nm; Rr = 52 nm | | MORg<br>Wg = 530 nm; Rg = 82 nm | | MORb<br>Wb = 458 nm; Rb = 108 nm | |
|---|---|---|---|---|---|---|
| N | NrWr − Rr | (Nr − 1) ·<br>Wr + Rr | Ng ·<br>Wg − Rg | (Ng − 1) ·<br>Wg + Rg | Nb ·<br>Wb − Rb | (Nb − 1) ·<br>Wb + Rb |
| 1 | 578 | 52 | 448 | 82 | 350 | 108 |
| 2 | 1208 | 682 | 978 | 612 | 808 | 566 |
| 3 | 1838 | 1312 | 1508 | 1142 | 1266 | 1024 |
| 4 | 2468 | 1942 | 2038 | 1672 | 1724 | 1482 |
| 5 | 3098 | 2572 | 2568 | 2202 | 2182 | 1940 |
| 6 | 3728 | 3202 | 3098 | 2732 | 2640 | 2398 |
| 7 | 4358 | 3832 | 3628 | 3262 | 3098 | 2856 |
| 8 | 4988 | 4462 | 4158 | 3792 | 3556 | 3314 |
| 9 | 5618 | 5092 | 4688 | 4322 | 4014 | 3772 |
| 10 | 6248 | 5722 | 5218 | 4852 | 4472 | 4230 |

There is no other value in the above table that is the same for all three wavelengths. However, several sets of values deserve a closer look:

a. MORr=578 nm; MORg=612 nm; and MORb=566 nm, where the largest difference is 46 nm.
b. MORr=1942 nm; MORg=2038 nm; and MORb=1940 nm where MORr≈MORb but where the largest difference is 98 nm.
c. MORr=2572 nm; MORg=2568 nm; and MORb=2640 nm where MORr≈MORg but where the largest difference is 72 nm.
d. MORr=3728 nm; MORg=3792 nm; and MORb=3772 nm where the largest difference is 64 nm.

While all four data sets can be eliminated from the theoretical point-of-view, in practice, the errors of the instrument may lead to confusion. For instance, in the last set of data, MORb=3772 is calculated from MORb=(Nb−1)·Wb+Rb=8Wb+Rb. Both Wb and Rb have errors in practice. If Wb has an error of ±5 nm, which is not unusual for a light source with temperature dependence, the MORb value would be in the range of 3772±40 nm, or 3732 nm to 3812 nm. Similarly, the MORr would be 3728±30 nm, or 3698 nm to 3758 nm; and MORg would be 3792±35 nm, or 3757 nm to 3827 nm. With just the assumed errors of wavelength instability, the values of MORr, MORg, and MORb would overlap, thus one cannot confidently eliminate this data set. Therefore, it might be more accurate to state that a given multi-order value can be stated to within "X" of accuracy, depending on the methodology used to establish the value, and the presence of wavelength instability or other variables. Step 4. In some cases, one can further distinguish false multi-order values from the true multi-order retardation value by using the Ar, Ag and Ab values. For each sampling point, the Ar, Ag and Ab values are either the same or different by 90°. In some cases, Ar, Ag and Ab data sets may provide distinctive patterns at two multi-order retardation values. Unfortunately, Ar, Ag and Ab data sets at multi-order retardation values of 3098 nm and 3772 nm are the same.

Figure 11:
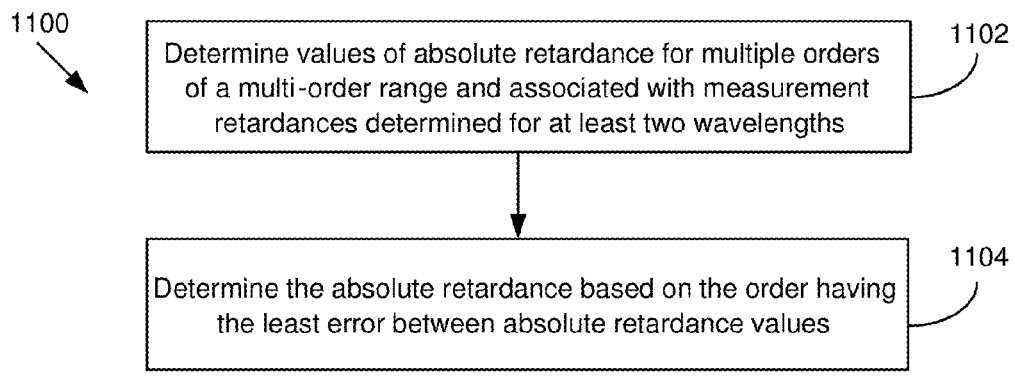

In FIG. 11, an example method 1100 for determining absolute retardance using Method Example IV and general example 800 is shown. At 1102, values of absolute retardance for multiple orders of a multi-order range and associated with the measurement retardances determined for at least two wavelengths are determined. At 1104, absolute retardance is determined based on the order having the least error between absolute retardance values.

Comparison of Different Example Methods II-IV and Combinations of Those Methods

Generally speaking, Method II has the least computation and it is thus the fastest method. It provides accurate results in all the regions listed in Table I except where two regions connect. Method IV is the simplest in logic and it provides accurate measurement in the full range, but it requires the most computation.

Methods II and method IV may be combined so that only the connecting regions need to be recalculated for multi-order retardation. The most accurate results are thus obtained within the shortest time. The accuracy of connecting regions can also be improved with Method III. It will be appreciated by one of ordinary skill in the art that the relative accuracy of a given multi-order value can be affected or improved by the proficient application of one or more of the equations shown here.

While the present invention has been described in terms of preferred embodiments, it will be appreciated by one of ordinary skill in the art that modifications may be made without departing from the teachings and spirit of the foregoing.

What is claimed is:

1. A method for carrying out unambiguous retardance measurement of a sample, comprising:
   directing, through a polarization state generator, source light comprising at least two different wavelengths; and then
   directing the light though the sample; and then
   directing the light though a polarization state analyzer;
   directing the light that emanates from the polarization state analyzer to an imaging device thereby to detect the intensity of the light and calculate a measurable retardance for each of the at least two different wavelengths; and
   determining an absolute retardance of the sample based on the measurable retardance with at least one of the following equations:

$$\delta_A = m\pi + \delta_\lambda = 2\pi(\Delta nL/\lambda),$$

where $\delta_A$ is the absolute retardance, m is an integer order, $\delta_\lambda$ is the measurable retardance, $\Delta n$ is a birefringence of the sample, L is a thickness of the sample, and $\lambda$ is one of the at least two different wavelengths, $$\delta_{gn} = \text{cyc}[(m_g\pi + \delta_k)(\lambda_k/\lambda_n)],$$

where cyc is a cyclical function, $m_g$ is a selected integer order, $\delta_k$ is the measurable retardance at a wavelength $\lambda_k$ of the at least two different wavelengths, and $\delta_{gn}$ are expected retardances $\delta_{g2} \ldots \delta_{gN}$ at one or more of the other wavelengths of the at least two different wavelengths $\lambda_n$, $$\epsilon_n = (\Sigma(N, n \neq k, \delta_{\lambda,n} - \delta_{gn}))^{1/2},$$

where $\epsilon_n$ are error values between the expected retardances $\delta_{gn}$ and the measurable retardances $\delta_{\lambda,n}$ for the at least two different wavelengths, and $$\delta_{Ai} = m_i \pi + \delta_i,$$

where $m_i$ is an integer order associated with a smallest error, $\delta_i$ is the measurable retardance, and $\delta_{Ai}$ is an associated absolute retardance.

2. The method of claim 1, further comprising accounting for dispersion of the light by the sample.

3. The method of claim 1, further comprising accounting for or preventing wavelength fluctuations attributable to temperature variations of the source light.

4. A method for measuring absolute retardance of an optical sample, comprising:
  directing light comprising a plurality of wavelengths through a polarization state generator source, the optical sample, and a polarization state analyzer;
  detecting, at an imaging device, retardance measurement light emanating from the optical sample after also passing through the polarization state analyzer at the plurality of wavelengths;
  determining a measurement retardance associated with the detected retardance measurement light at each of the wavelengths; and
  determining an absolute retardance associated with the optical sample based on the measurement retardances determined at each of the wavelengths.

5. The method of claim 4, wherein the optical sample has an arbitrary fast axis orientation with respect to the retardance measurement light directed to the optical sample.

6. The method of claim 4, wherein the retardance measurement light extends over the optical sample so that the determined absolute retardance forms an absolute retardance image associated with a measurement area of the optical sample.

7. The method of claim 6, further comprising:
  directing the retardance measurement light to multiple positions of the optical sample; and
  forming an absolute retardance image based the absolute retardance determined at each of the positions.

8. The method of claim 7, wherein the retardance image has a retardance resolution extending over multiple orders.

9. The method of claim 4, further comprising measuring an optical intensity of the received retardance measurement light wherein the measurement retardance at each of the wavelengths is determined based on the measured intensity.

10. The method of claim 4, wherein the determining the absolute retardance associated with the optical sample based on the measurement retardances determined at the wavelengths comprises:
  determining a plurality of expected retardances, each expected retardance corresponding to a wavelength of the plurality of wavelengths and being based on the measurement retardance determined for a selected wavelength of the plurality of wavelengths that is different from the wavelength corresponding to the expected retardance and being further based on one or more absolute retardance order estimates associated with an absolute retardance range;
  determining a plurality of error values associated with one or more wavelengths of the plurality of wavelengths by comparing the expected retardances with the measurement retardances; and
  determining the absolute retardance based on an absolute retardance order associated with a lowest error value of the plurality of error values for at least one of the plurality of wavelengths.

11. The method of claim 10, further comprising:
  averaging the absolute retardances determined for more than one wavelength of the plurality of wavelengths.

12. The method of claim 10, wherein the expected retardances are scaled according to a dispersion aspect of the optical sample.

13. The method of claim 4, wherein the determining the absolute retardance associated with the optical sample based on the measurement retardances determined at the wavelengths includes:
  determining sum and difference retardances corresponding to at least two of the wavelengths based on a measurement retardance profile for the at least two wavelengths over an absolute retardance range;
  based on the sum and difference retardances, tabulating absolute retardance conditions over the absolute retardance range, the absolute retardance conditions including absolute retardance order values and measurement retardance signs associated with the at least two wavelengths; and
  determining the absolute retardance based on the determined measurement retardances and the tabulated absolute retardance conditions.

14. The method of claim 13, further comprising determining a fast axis angle based on retardance remainders corresponding to the determined absolute retardance of the at least two wavelengths.

15. The method of claim 13, wherein the at least two wavelengths is three or more wavelengths and the absolute retardance is further determined by averaging the absolute retardances determined from at least two pairs of the three or more wavelengths.

16. The method of claim 4, wherein the determining the absolute retardance associated with the optical sample based on the measurement retardances determined at the wavelengths includes:
  determining values of absolute retardance for multiple orders of a multi-order range and associated with the measurement retardances determined for at least two of the wavelengths; and
  determining the absolute retardance based on the order having the least error between absolute retardance values.

17. The method of claim 16, wherein the absolute retardance is provided with an error margin associated with wavelength variability of the retardance measurement light.

18. The method of claim 16, further comprising:
  determining a fast axis angle based on the measurement retardance at each wavelength;
  wherein determining the absolute retardance based on the order having the least error between retardance values includes distinguishing false absolute retardance values based on the determined fast axis angles.

19. The method of claim 13, further comprising, for measurement retardances corresponding to a sum and difference retardance near a retardance connecting region:
  determining values of absolute retardance for multiple orders of a multi-order range and associated with the measurement retardances determined for at least two of the wavelengths; and
  determining the absolute retardance based on the order having the least error between absolute retardance values.

20. A system, comprising:
- a light source configured to generate light at a plurality of wavelengths;
- a polarization state generator configured to receive light from the light source and generate retardance measurement light having different polarization states;
- a sample positioned to have its retardance measured by the retardance measurement light;
- a polarization state analyzer configured to receive the retardance measurement light emanating from the sample;
- an imaging device configured to measure intensity of the retardance measurement light from the polarization state analyzer with different polarization states; and
- a retardance measurement system in communication with the imaging device and being programmed or configured to:
  - determine a measurement retardance associated with the detected measurement light at each of the wavelengths; and
  - determine an absolute retardance associated with the sample based on the measurement retardances determined at each of the wavelengths.

\* \* \* \* \*